(12) United States Patent
Martin

(10) Patent No.: US 6,199,262 B1
(45) Date of Patent: Mar. 13, 2001

(54) METHOD OF MAKING A GUIDING CATHETER

(75) Inventor: Brian B. Martin, Boulder Creek, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/258,657

(22) Filed: Feb. 26, 1999

Related U.S. Application Data

(62) Division of application No. 08/915,360, filed on Aug. 20, 1997, now Pat. No. 5,902,287.

(51) Int. Cl.[7] .................................................... B23P 11/00
(52) U.S. Cl. .................... 29/525.15; 156/293; 156/257; 264/544; 604/532; 604/525
(58) Field of Search ................................ 264/544, 264; 604/526, 532, 525; 156/256, 257, 293, 73.1, 308.2, 308.4; 29/469.5, 525.15

(56) References Cited

U.S. PATENT DOCUMENTS

| | | |
|---|---|---|
| 3,752,617 * | 8/1973 | Burlis et al. . |
| 4,469,483 | 9/1984 | Becker et al. . |
| 4,576,772 * | 3/1986 | Carpenter . |
| 4,590,028 * | 5/1986 | Rosenkrantz et al. ............... 264/154 |
| 4,761,871 * | 8/1988 | O'Connor et al. .............. 29/431.2 X |
| 4,776,846 | 10/1988 | Wells . |
| 4,822,345 | 4/1989 | Danforth . |
| 4,909,787 | 3/1990 | Danforth . |
| 4,976,691 | 12/1990 | Sahota . |
| 5,368,564 | 11/1994 | Savage . |
| 5,378,234 | 1/1995 | Hammerslag et al. . |
| 5,437,632 | 8/1995 | Engelson . |
| 5,453,099 | 9/1995 | Lee et al. . |
| 5,456,674 | 10/1995 | Bos et al. . |
| 5,470,322 | 11/1995 | Horzewski et al. . |
| 5,772,641 * | 6/1998 | Wilson . |
| 5,849,035 * | 12/1998 | Pathak et al. . |
| 5,868,718 * | 2/1999 | Pepin et al. . |
| 5,902,287 * | 5/1999 | Martin . |
| 6,110,164 * | 8/2000 | Vidlund . |

* cited by examiner

*Primary Examiner*—S. Thomas Hughes
*Assistant Examiner*—Steven A Blount

(57) ABSTRACT

A method of making a catheter, including an elongated tube structure having a proximal end and at least one preset curved portion proximate a distal end. The preset curved portion includes a first material located generally along an outer surface of the preset curved portion and a second material located generally along an inside surface of the preset curved portion. The first material preferably has a greater stiffness than the second material, so that the catheter is capable of assuming a generally straight configuration without plastic deformation.

15 Claims, 3 Drawing Sheets

METHOD OF MAKING A GUIDING CATHETER

This is a division of application Ser. No. 08/915,360, filed Aug. 20, 1997, now U.S. Pat. No. 5,902,287, which is incorporated herein by reference.

FIELD THE INVENTION

The present invention relates to a guiding catheter that combines stiffness that resists bending stress or torque and elasticity that permits straightening without plastic deformation.

BACKGROUND OF INVENTION

Medical catheters generally comprise elongated tube like members which may be inserted into the body either percutaneously, or via a body orifice, for any of a wide variety of diagnostic and therapeutic purposes. Such medical applications generally require the use of a catheter having the ability to turn corners, such as in ocular irrigation or aspiration applications, or to negotiate twists and turns, such as in certain cardiovascular applications.

Catheters are typically introduced to the patients body through an introducer sheath. The catheter must generally be straightened to fit through the introducer sheath. Therefore, the catheter must be constructed so that it is elastically resilient enough to go through the introducer sheath without plastic deformation, yet resilient enough to meet the performance needs of the particular medical procedure.

For some applications, an inner catheter having a preformed shape is straightened and placed in an outer guiding sheath. When the inner catheter is extended or the outer sheath withdrawn, the inner catheter assumes its original shape. Again, the inner catheter must be constructed so that it is elastically resilient enough to straighten without plastic deformation, yet resume its original configuration when the outer sheath is removed.

For example, percutaneous translumenal coronary angioplasty (PTCA) requires manipulation of a catheter from a proximal position outside the patient's body through branched or tortuous portions of the patients arterial system for purposes of alleviating an obstruction by inflating a balloon. This particular procedure has been performed with increasing frequency over the past years in preference to open heart bypass surgery.

FIG. 1 illustrates the typical configuration of a conventional left coronary guiding catheter 20 with a dilation balloon 24 in the aorta when engaged with a stenosis 24 in the left main coronary artery during the performance of left coronary artery PTCA. The application of force 22 to advance a dilation balloon across the region of stenosis 26 increases the bending stress 28 on the bend 30 of the guiding catheter 20. The pre-bent configuration of the guiding catheter 20, in this situation a left Judkin's configuration, is unable to overcome the resistance at the stenosis 24, causing distal end 32 to back away from the entrance of the left main coronary artery and the angioplasty balloon catheter 24 to prolapse in the accenting aorta, precluding further progress.

Inability to advance the angioplasty balloon across the coronary stenosis because of instability of the guiding catheter and subsequent prolapse of the angioplasty balloon catheter represents one of the most common reasons for failure during the performance of a coronary angioplasty procedure. The guiding catheter disengages in this circumstance because of its flexibility. The guiding catheter has intrinsic flexibility because it must conform to the configuration of the aorta and aortic arch, which contain both linear and curved segments, during introduction. Insertion of the guiding catheter requires that it be advanced over a guidewire up the aorta, which is relatively straight, and then over the aortic arch, which, as the name implies, is curvilinear.

The stability afforded by guiding catheters typically relates to the limited intrinsic stiffness of these catheters. The stiffness of these prior guiding catheters is subject to a "warm-up" phenomenon (becoming more flexible as they remain in the body and equilibrate to body temperature) and thus varies inversely with the temperature of the device. Hence, these catheters tend to be particularly stiff on introduction into the body, when flexibility is preferable, and yet relatively flexible and hence unstable following exposure to body temperatures during balloon catheter manipulation across a coronary stenosis when rigidity is preferable.

U.S. Pat. No. 4,909,787 (Danforth) discloses a catheter having a closed chamber eccentrically disposed along almost the entire length of the housing such that it virtually encompasses the housing. The catheter preferably contains a relatively elastic segment disposed preferentially along the outer circumference of the curvature of the catheter. The chamber may be filled with a fluid. The catheter is capable of asymmetric elongation when hydrostatic pressure is applied to the chamber, resulting in the development of bending stress and increased rigidity on the distal end as desired by the operator.

U.S. Pat. No. 5,456,674 (Bos et al.) discloses a catheter with variable longitudinal properties. The catheters are manufactured by simultaneously conveying a plurality of streams of different materials to a molding nozzle and merging the streams together to form a catheter. The catheter is manufactured with varying properties along its longitudinal axis corresponding to properties of the constituent streams of materials.

SUMMARY OF THE INVENTION

The present invention relates to a catheter comprising an elongated tube structure having a proximal end and at least one preset curved portion proximate a distal end. The preset curved portion comprising a first material located generally along an outer surface on the outer radius of the preset curved portion and a second material located generally along an inner surface on the inner radius of the preset curved portion. The present catheter is particularly useful as a guiding catheter that combines stiffness to resist bending stress and elasticity to permit straightening without plastic deformation.

The first material preferably has a modulus of elasticity greater than the modulus of elasticity of the second material. Alternatively, the modulus of elasticity of the second material may be greater than a modulus of elasticity of the first material. The first material preferably has a first stiffness greater than a second stiffness of the second material. A third material may be interposed between the first and second materials. The third material preferably has a third stiffness less than the first stiffness, but greater than the second stiffness.

The preset curved portion is capable of assuming a generally straight configuration without plastic deformation. The cross sectional area of at least a portion of the preset curved portion is about 50% of the first material and about 50% of the second material. The first and the second materials are preferably coextruded structure. Alternatively, the first material is bonded to the second material. An outer resilient layer may alternatively extend around the first and second materials. In one embodiment, the one preset curved portion has a bend configuration suitable for performing percutaneous coronary angioplasty.

The present invention is also directed to a method of forming a catheter. The method includes the step of forming an elongated tube structure having a proximal end and at least one preset curved portion proximate a distal end. The preset curved portion comprises a first material located generally along an outer surface of the preset curved portion and a second material located generally along an inside surface of the preset curved portion. In one embodiment, the step of forming the elongated tube structure includes interposing a third material between the first and second materials. The tube structure may be formed by coextrusion or joining discrete segments of material.

Stiffness refers to the ratio of a steady force acting on a deformable elastic medium to the resulting displacement. The modulus of elasticity refers to the ratio of the increment of some specified form of stress to the increment of some specified form of strain. In the catheter art, torque generally refers to a force that causes a catheter to kink or twist (torque failure). Bending stress refers to an internal tensile or compressive longitudinal stress developed in a member in response to a curvature induced by an external load or force.

DETAILED DESCRIPTION OF THE INVENTION

Figure 1:
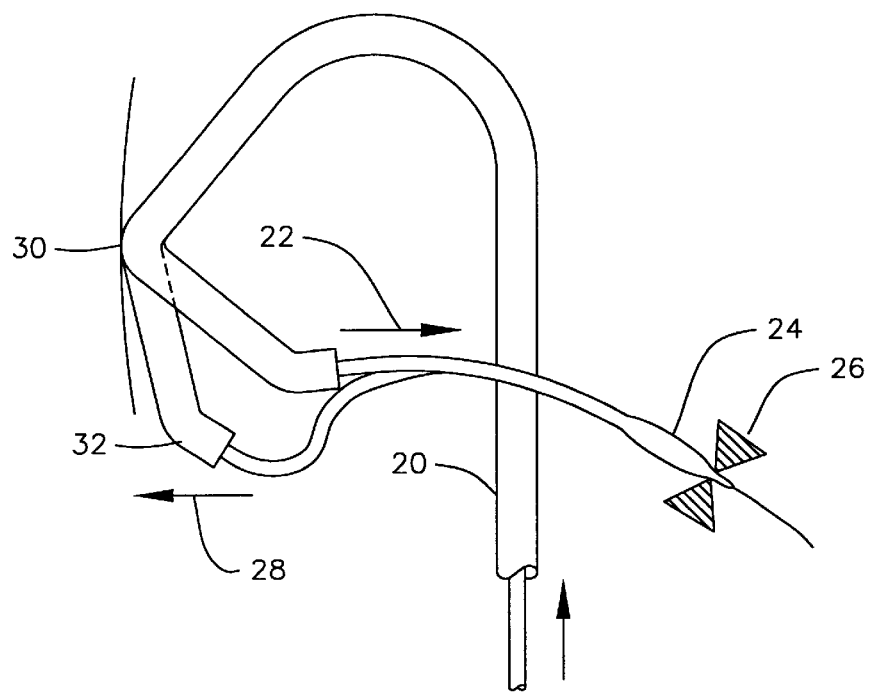
FIG. 1 is schematic illustration of the force that develops within a guiding catheter as an angioplasty dilation balloon catheter advances within the left coronary artery.
Figure 2:
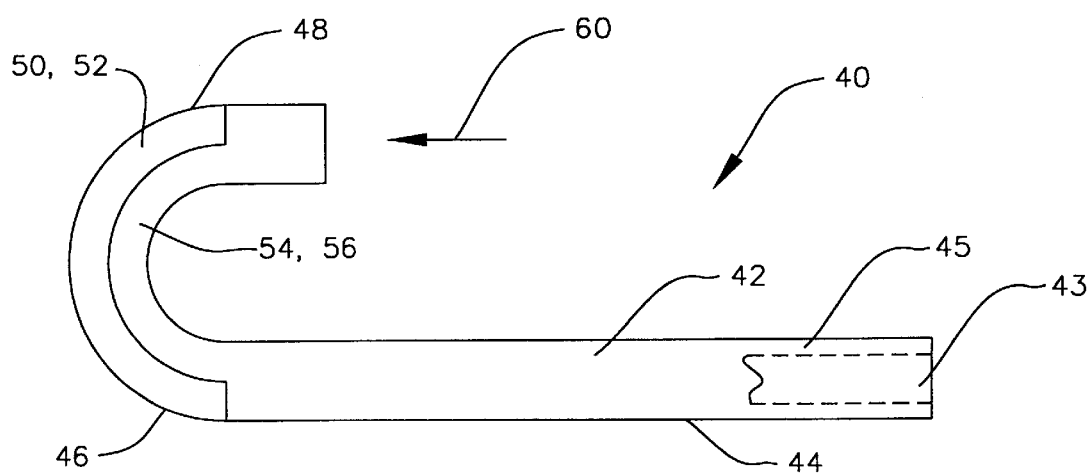
FIG. 2 is a side view of a guiding catheter according to the present invention.
Figure 3:
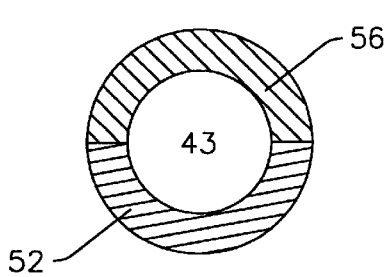
FIG. 3 is a cross sectional view of the guiding catheter of FIG. 2.

FIGS. 2 and 3 illustrate an exemplary catheter 40 made according to the present invention. The catheter 40 includes an elongated structure 42 forming a lumen 43 which is generally straight along a proximal portion 44. At least one preset curved portion 46 is located along a distal portion 48. The lumen 43 continues through the distal portion 48 of the elongated structure 42. An outer surface 50 located generally along the outer radius of the preset curved portion 46 is preferably constructed of a first material 52. An inner surface 54 located generally along the inner radius of the preset curved portion 46 is constructed of a second material 56. In the embodiment of FIGS. 2 and 3, the proximal portion 44 is also constructed from the second material.

The first material preferably has a greater stiffness (higher modulus of elasticity), and hence a greater resistance to bending stress or torque than the more elastic second material. Consequently, locating of the first material 52 along the outer surface 50 reinforces the preset curved portion 46 so that it is better able to generally retain its shape even when subjected to a force 60. In an alternate embodiment, the locations of the first and second materials 52, 56 may be reversed.

Figure 5B:
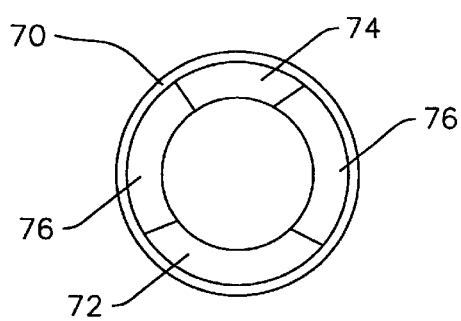
FIG. 5B is a cross sectional view of the guiding catheter of FIG. 5A.
Figure 5A:
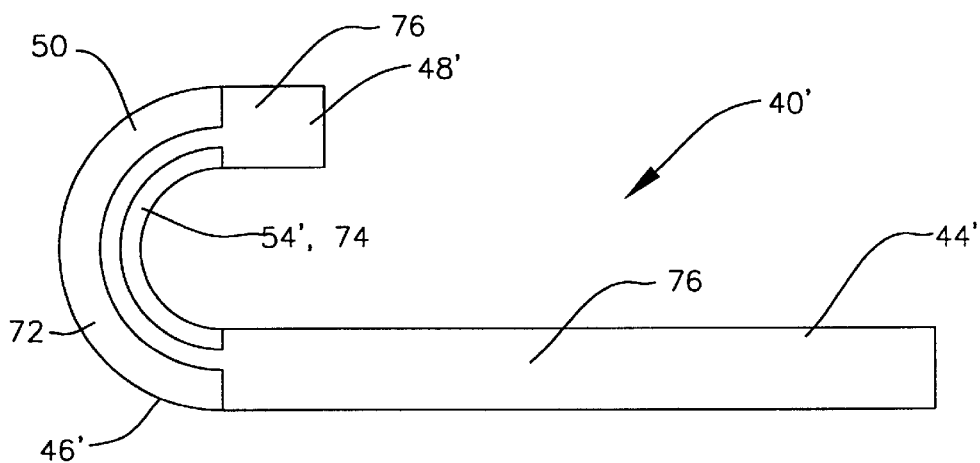
FIG. 5A is a side view of an alternate guiding catheter according to the present invention.

As best illustrated in FIG. 3, the first material 52 accounts for about 50% of the cross sectional area of the catheter 40 and the second material 56 accounts for the other 50%. It will be understood that the ratio of the first material to the second material can vary depending on the design and application of the catheter 40, such as illustrated in FIGS. 5A and 5B. Additionally, it is possible that more than two different materials can be used for forming the present catheter. The first and second materials 52, 56 are preferably of different colors so that the operator can distinguish the stiffer portion from the more elastic portion.

The present catheter achieves a useful balance of rigidity and flexibility with relatively thin wall thicknesses. Thinner walls 45 permits a larger inner lumen for a corresponding outer diameter. Although the thickness of the walls 45 will vary with the application of catheter 40, the wall thickness for a guiding catheter used for PTCA applications may be in the range of about 0.1 to 0.31 mm (0.004 to 0.012 inches). The lumen is preferably about 1.0 to 3.5 mm (0.038 to 0.138 inches).

A variety of polymeric material may be used for the present guiding catheter, such as polyethylene, polypropylene, polyurethane, polyesters. In one embodiment, Pebax 7233 may be used for the first material 52 and Pebax 6333 may be used for the second material 56. Pebax polymers are available from Elf Atochem located in Philadelphia, Pa. It will be understood that components of the catheter, (i.e., first and second materials) are preferably sufficiently compatible to be bonded together using adhesives, ultrasonic welding, heat fusion or coextrusion. Otherwise, the catheter designer is free to select polymers that provide the optimum balance of stiffness and elasticity.

Figure 4:
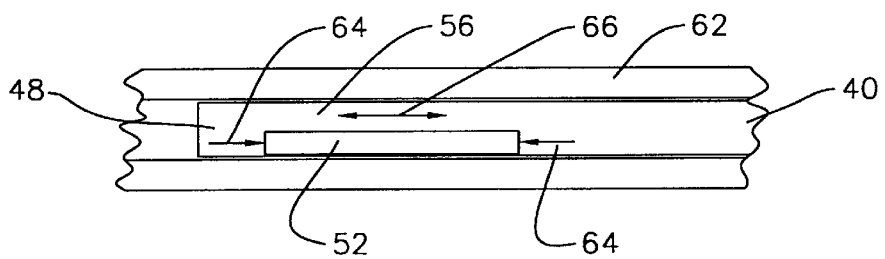
FIG. 4 is a side sectional view of the guiding catheter of FIG. 1 passing through an introducer sheath.

FIG. 4 is a sectional view of the present catheter 40 passing through an introducer sheath 62. The less elastic first material 52 is subjected to compressive forces 64 while the more elastic second material 56 is subjected to tensile forces 66. Once the catheter 40 is removed from the introducer sheath 62, the preset curved portion will resume substantially its original shape. The compressive force 64 and tensile force 66 are preferably within the elastic range of the materials 52, 56. The first material 52 preferably responds with resiliency to compressive forces and the second material 56 preferably responds resiliently to tensile forces. Resilience refers to the ability of a strained body, by virtue of high yield strength and relatively low elastic modulus, to recover its size and form following deformation. It will be understood, however, that for some applications it may be desirable to subject the first material 52 and/or the second material 56 to forces sufficient to cause plastic deformation.

FIGS. 5A and 5B illustrate an altered catheter 40' constructed according to the present invention. The outer surface 50' of the preset curved portion 46' is constructed of a first material 72. The inner surface 54' of the preset curved portion 46' is constructed of a second material 74. A region between the first material and second material 72, 74 is constructed of a third material 76, which also forms the proximal portion 44' and the distal end 48' of the catheter 40'. In one embodiment, the second material 74 has the highest elasticity and the first material 72 the lowest elasticity (greatest stiffness), while the third material 76 has an intermediate level of elasticity. As illustrated in FIG. 5B, an elastic reinforcing member 70 may optionally extend around the preset curved portion 46' of the guiding catheter 40'.

Figure 6:
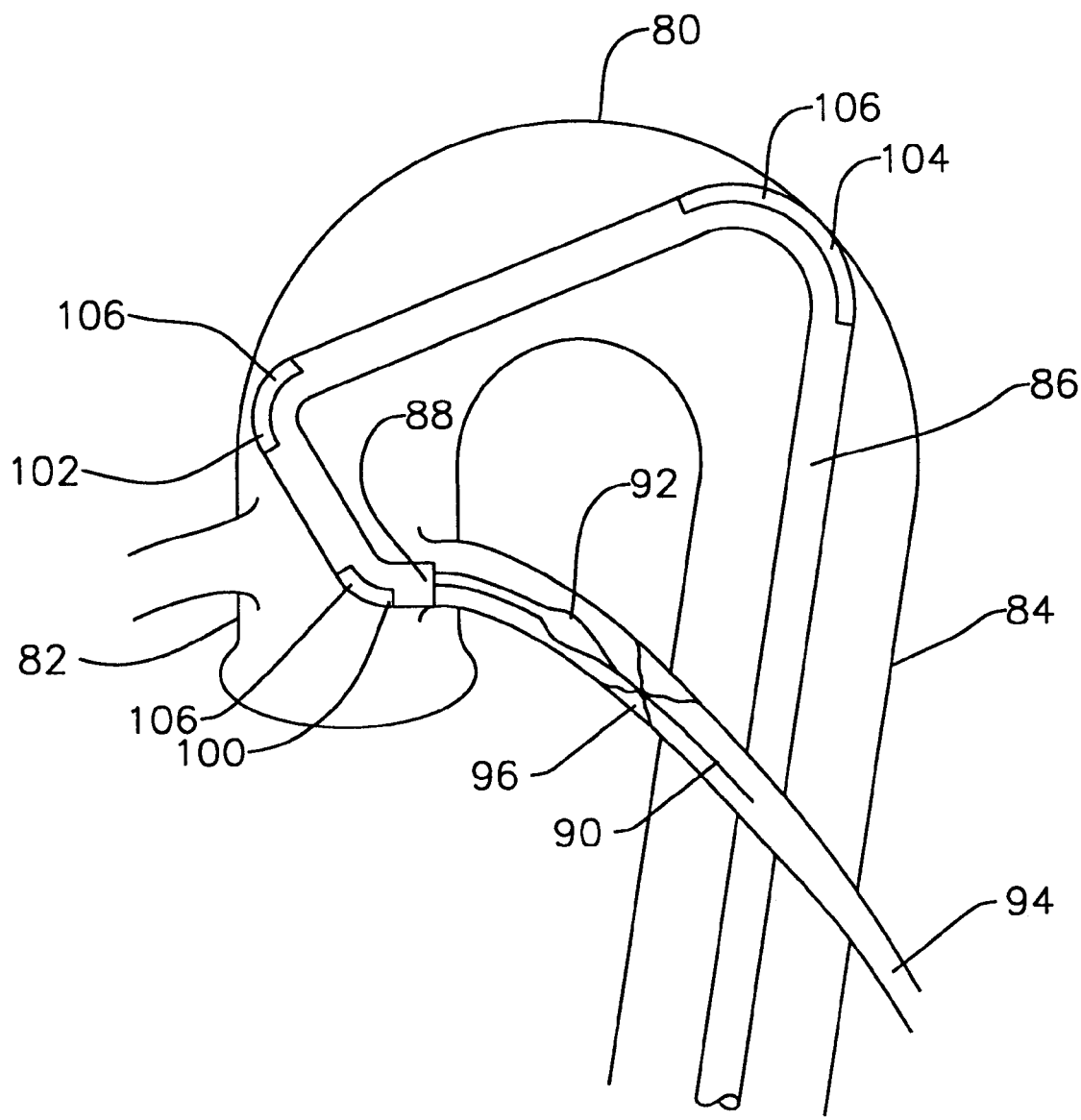
FIG. 6 is a schematic illustration of a guiding catheter according to the present invention engaged with the left main coronary artery for manipulation of an angioplasty dilation balloon catheter across a region of stenosis.

FIG. 6 is an illustration of the present guiding catheter configured for performing percutaneous transluminal coronary angioplasty of the left main coronary artery. Although FIG. 6 illustrates a left Judkin's configuration guiding catheter, the invention is not confined to this configuration. The present guiding catheter can be applied to all configurations of guiding catheters including left and right Judkin's, Sone's, Stertzer and Amplatz configurations. Related procedures that may utilize the present guiding catheter include laser angioplasty, angioscopy or atherectomy.

The aorta 80 includes ascending portion 82 and a descending portion 84. The guiding catheter 86 is manipulated up the descending aorta 84 and down the ascending aorta 82 so that the distal end 88 is within the coronar ostium, thus permitting subsequent advancement of the angioplasty guide wire 90 and the balloon catheter 92 within the diseased vessel 94.

Advancement of the balloon catheter 92 is typically resisted by regions of stenosis 96 in the diseased vessel 94. This resistance creates bending stress on the guiding catheter 86, causing the preset curved portions 100, 102, 104 to deform. The preset curved portions 100–104 may be constructed to have a less elastic first material 106 located along the outer surface in each of the curves 100–104. During use of the guiding catheter 86, the less elastic material 106 resists the compressive force associated with the bending stress generated by resistance to advancement of the balloon catheter 92. The material 108 on the inside surface of the curve 100–104 preferably has a greater elasticity than the material 106 to facilitate introduction and removal of the guiding catheter 86 from the patient (see FIG. 4).

Existing catheters are generally made as stiff as possible, while still providing sufficient elasticity to permit the catheter to be inserted through an introducer sheath. As a result of the required elasticity, some catheters lack adequate stiffness to effectively perform certain procedures once introduced into the body. The present guiding catheter provides sufficient stiffness to facilitate medical procedures, while minimizing the potential for catheter-induced vascular trauma associated with the introduction of the catheter.

The present guiding catheter resists considerable bending stress at the distal aspect of the catheter to preserve the engagement of the guiding catheter within the coronary ostium during manipulation of the dilation balloon catheter. The incidence of vascular trauma sustained during catheter introduction varies directly as a function of the relative stiffness of the catheter. The enhanced stability afforded by the present guiding catheter circumvents the need to force a relatively rigid guiding catheters of the prior art deep within a coronary lumen to achieve stability, as well as the need for the sequential balloon technique. Thus, the flexibility of the present catheter contributes to the safety of the procedure during both catheter introduction and balloon catheter manipulation.

The catheter of the present invention may be constructed from a variety of techniques. The outer and inner surfaces 50, 54 may be assembled from segments of a tube structure using various bonding techniques, such as ultrasonic welding, heat fusion or adhesives. In an embodiment where the guiding catheter is constructed from multiple discrete segments, an outer reinforcing member 70 may be used to temporarily secure the components in place or as a permanent covering for the catheter 40'. The reinforcing member 70 permits the use of materials that are incompatible or otherwise do not adequately bond by adhesives or during coextrusion. In another embodiment of the present method, the first and second materials of the present catheter may be coextruded using various methods, such as disclosed in U.S. Pat. No. 5,456,674 (Bos et al.).

The present method of coextrusion comprises forming an elongated tube structure from first and second materials. In one embodiment, it is possible to interpose a third material between the first and second materials. The proximal and distal ends of the catheter may also be constructed from the third material. The ratio of the various materials may be adjusted during the coextrusion process.

At least one preset curved portion is formed, preferably by thermoforming, proximate the distal end so that the less elastic first material located generally along an outer surface of the preset curved portion and the more elastic second material is located generally along an inside surface of the preset curved portion. The distal end of the catheter may be formed into a variety of preformed shapes, such as a shape suitable for performing percutaneous coronary angioplasty.

By selecting the first material to have a first stiffness greater than a second stiffness of the second material, the preset curved portion is capable of resisting bending stress applied thereto, while being capable of assuming a generally straight configuration without plastic deformation. The coextrusion process permits that ratio of the two or more materials in the cross section of the catheter to vary according to design requirements.

Patents and patent applications disclosed herein, including those disclosed in the background of the invention, are hereby incorporated by reference. Other embodiments of the invention are possible. It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method of manufacturing a catheter, the method comprising:

forming an elongated tube structure comprising a proximal end, a distal end and at least one preset curved portion located between the proximal end and the distal end, the elongated tube structure comprising a first material and a second material, wherein the method further comprises:

locating the first material along the preset curved portion, wherein the first material extends proximally and distally along the preset curved portion; and locating the second material along the preset curved portion, wherein the second material extends proximally and distally along the preset curved portion, and further wherein the second material extends beyond the first material both proximally and distally.

2. The method of claim 1 wherein the first material comprises a modulus of elasticity greater than a modulus of activity of the second material.

3. The method of claim 1 wherein the second material comprises a modulus of elasticity greater than a modulus of elasticity of the first material.

4. The method of claim 1 wherein the first material comprises a first stiffness and the second material comprises a second stiffness less than the first stiffness.

5. The method of claim 1 further comprising locating a third material between the first and second materials.

6. The method of claim 5 wherein the first material comprises a first stiffness, the second material comprises a second stiffness less than the first stiffness, and the third material comprises a third stiffness less than the first stiffness but greater than the second stiffness.

7. The method of claim 1 wherein at least a portion of the preset curved portion of the catheter has a cross sectional area comprising about 50% of the first material and about 50% of the second material.

8. The method of claim 1 wherein manufacturing the catheter comprises coextruding the first and second materials.

9. The method of claim 1 wherein manufacturing the catheter comprises attaching the first material to the second material by ultrasonic welding.

10. The method of claim 1 wherein manufacturing the catheter comprises fusing the first material to the second material.

11. The method of claim 1 wherein manufacturing the catheter comprises adhesively attaching the first material to the second material.

12. The method of claim 1 wherein the at least one preset curved portion is formed by thermoforming.

13. The method of claim 1 further comprising securing the first and second materials with an outer reinforcing member.

14. A method of manufacturing a catheter, the method comprising:

forming an elongated tube structure comprising a proximal end, a distal end and at least one preset curved portion located between the proximal end and the distal end, the elongated tube structure comprising a first material having a first stiffness and a second material having a second stiffness less than the first stiffness, wherein the method further comprises:

locating the first material along the preset curved portion such that it extends both proximally and distally along the preset curved portion; and locating the second material along the preset curved portion so that the catheter is capable of assuming a generally straight configuration without plastic deformation, the second material extending both proximally and distally from the preset curved portion such that it extends beyond the first material both proximally and distally.

15. A method of manufacturing a catheter, the method comprising:

forming an elongated tube structure comprising a proximal end, a distal end and at least one preset curved portion located between the proximal end and the distal end, the elongated tube structure comprising a first material, a second material, and a third material, wherein the method further comprises:

locating the first material along the preset curved portion, wherein the first material extends proximally and distally along the preset curved portion;

locating the second material along the preset curved portion, wherein the second material extends proximally and distally along the preset curved portion, and further wherein the second material extends beyond the first material both proximally and distally; and locating the third material between the first material and the second material.

* * * * *